United States Patent [19]

Zinder et al.

[11] Patent Number: 4,595,658
[45] Date of Patent: Jun. 17, 1986

[54] METHOD FOR FACILITATING EXTERNALIZATION OF PROTEINS SYNTHESIZED IN BACTERIA

[75] Inventors: Norman D. Zinder; Peter Model, both of New York, N.Y.; Jef D. Boeke, Cambridge, Mass.

[73] Assignee: The Rockefeller University, New York, N.Y.

[21] Appl. No.: 416,922

[22] Filed: Sep. 13, 1982

[51] Int. Cl.$^4$ .................. C12P 21/00; C12P 21/06; C12P 21/02; C12P 21/04; C12N 15/00; C12N 1/20; C12N 1/02; C12N 1/00; C12R 1/19

[52] U.S. Cl. .................................. 435/68; 435/70; 435/71; 435/172.3; 435/253; 435/261; 435/317; 435/849; 435/69; 935/29; 935/47; 935/48; 935/73

[58] Field of Search .............. 435/68, 70, 172, 253, 435/317, 172.3; 935/31, 47, 48

[56] References Cited

U.S. PATENT DOCUMENTS 4,336,336 6/1982 Silhavy et al. ................. 435/172
4,338,397 7/1982 Gilbert et al. ................... 435/68

FOREIGN PATENT DOCUMENTS 0006694 8/1980 European Pat. Off. .

OTHER PUBLICATIONS

Webster et al.: in *The Single-Stranded DNA Phages*, Denhardt et al. (Ed.), Cold Spring Harbor Laboratory, 1978, pp. 557–569.
Horiuchi et al.: in *The Single-Stranded DNA Phages*, Denhardt et al. (Ed.), Cold Spring Harbor Laboratory, 1978, pp. 113–137.
Villa–Komaroff et al.: Proc. Nat'l. Acad. Sci. USA 75, 3727 (1978).
Talmadge et al.: Gene 12, 235 (1980).
Nielsen et al.: ASM News 49(7), 318 (1983).
Lazzaroni et al.: J. Bacteriol. 145, 1351 (1981).
Holland: Nature 308, 120 (1984).
Silhavy et al.: "A Genetic Approach to the Study of Protein Localization in *Escherichia coli*", p. 204.
Strickberger: *Genetics*, 2nd Ed., MacMillan, New York, p. 577.
Lopes et al.: J. Bacteriol. 109, 520 (1972).
Anderson et al.: J. Bacteriol. 140, 351 (1979).
Fraser: *CRC Critical Reviews in Food Science and Nutrition* (1982).
Beck et al.: Gene 16, 35 (1981).

*Primary Examiner*—Lionel M. Shapiro
*Assistant Examiner*—James Martinell
*Attorney, Agent, or Firm*—Pennie & Edmonds

[57] ABSTRACT

A method of externalizing proteins from the periplasmic space of gram-negative bacteria and in particular, *E. coli* and its relatives, comprising utilizing bacteria which have a phage gene, coding for a protein (such as gene III protein) or a mutant bacterial gene (such as a gene coding for a membrane function) which causes perturbation of the outer bacterial membrane resulting in leakage of proteins in the periplasmic space from the cell.

20 Claims, 2 Drawing Figures

METHOD FOR FACILITATING EXTERNALIZATION OF PROTEINS SYNTHESIZED IN BACTERIA

TABLE OF CONTENTS

1. Field of the Invention
2. Background of the Invention
3. Brief Summary of the Invention
4. Detailed Description of the Invention
   4.1 Identification and Isolation of Gene III
   4.2 Insertion into a Cloning Vector
   4.3 Expression of Gene III
   4.4 Effects of Gene III Expression
      4.4.1 Increased Colicin Tolerance
      4.4.2 Increased Deoxycholate Sensitivity
      4.4.3 Decreased Ability to Form Functional F-Pili
      4.4.4 Leakage of Proteins from the Periplasm

1. FIELD OF THE INVENTION

The invention described herein was made in the course of work supported in part by grants from the National Science Foundation and the National Institutes of Health.

This invention relates to the externalization of proteins from the periplasmic space of gram-negative bacteria and, in particular, E. coli and its relatives to the exterior of the cells owing to the presence and expression of a phage gene, or a portion thereof, coding for a protein (such as f1 bacteriophage gene III protein), or any mutant bacterial gene coding for a protein (such as, for example, a gene coding for a membrane function) which causes perturbation of the outer bacterial membrane resulting in leakage of proteins in the periplasmic space from the cell. Periplasmic proteins are extracytoplasmic proteins located between the inner and outer membranes of E. coli and other gram-negative bacterial cells. These proteins include any protein that is transported to the periplasmic space by known techniques of genetic engineering as well as proteins naturally located in the periplasmic space. Therefore, the method of this invention can be used to isolate more readily and efficiently any protein attached to an appropriate leader sequence which mediates transport of the protein to the periplasmic space or any naturally occurring bacterial periplasmic proteins (such as those involved in bacterial transport). Perturbation of the outer membrane by a phage protein or defective bacterial protein that causes the membrane effect allows leakage and collection of both types of protein. In the preferred embodiment of the invention, f1 bacteriophage gene III protein may be produced in the cell by insertion of the phage gene III into a plasmid or bacterial chromosome. In another embodiment of the invention, a bacterial mutant that leaks periplasmic proteins may be utilized to isolate proteins transported to the periplasm by genetic engineering techniques.

2. BACKGROUND OF THE INVENTION

By definition, the existence of periplasmic proteins requires some mechanism for the translocation of these proteins from the cytoplasm where they are synthesized through the cytoplasmic membrane to the periplasmic space. Often, when the bacterial cell synthesizes one of these extracytoplasmic proteins, the final form of the protein (the "mature protein") is synthesized with a peptide presequence (the "leader sequence") linked by a peptide bond to the amino terminus of the mature protein. The protein molecule with the leader sequence attached to the mature protein is called the "precursor protein". This leader sequence is essential to the transport of many extracytoplasmio proteins across membrane surfaces and is cleaved from the molecule at some point during the transport process, thus releasing the mature protein. In E. coli, for example, periplasmic proteins found to contain such leader sequences include β-lactamase, alkaline phosphatase as well as a peptidase and a protease.

The leader sequences of many E. coli extracytoplasmic proteins have been analyzed and a common structure has emerged. The amino terminal ends of the leader sequences are basic in nature and are followed by a highly hydrophobic region. From this and other research two models have been proposed to explain how the sequences may function in the transport of proteins across membrane surfaces.

According to the signal hypothesis of Blobel and Dobberstein [J. Cell Biol. 67: 835-851 (1975)] the hydrophobic region of the leader sequence of a nascent protein molecule acts to bind the protein-ribosome complex to the cytoplasmic membrane during formation of the protein. In binding to the membrane, the leader sequence interacts with a membrane receptor protein which is then activated to form a hydrophilic channel through the membrane into which the growing protein chain is inserted and through which it is translocated to the periplasm. At some point during this transport, the leader sequence is removed from the protein molecule and the mature protein appears in the periplasm.

The loop model of Inouye and Halegoua, [CRC Crit. Rev. Biochem 7: 339-371 (1980)] proposes that, as the extracytoplasmic protein is translated, the basic amino terminal region of the leader sequence binds onto the membrane, its basic amino acid residues interacting with the negatively charged membrane surface. The hydrophobic region of the sequence is then inserted into the membrane forming a loop and interacting with the lipid that comprises a large part of the membrane. As translation proceeds, the looped leader sequence traverses the membrane and is cleaved, leaving a track through which the nascent protein can move (as it is formed) through the membrane to the periplasm.

In recent years, researchers have attempted to utilize the translation and transport mechanisms in E. coli to produce and obtain proteins not normally produced by the microorganism, including proteins of other bacteria and proteins of viruses and higher organisms. These proteins not native to E. coli are called "foreign" proteins. One technique involves insertion of a DNA sequence coding for a "foreign" protein of interest (e.g., a eukaryotic protein) at some point after the leader sequence (i.e., distal to the carboxy terminus of the leader sequence) of a bacterial gene coding for the precursor form of an extracytoplasmic protein. The protein resulting from such a constructed gene is called a "fusion protein" consisting of a foreign protein usually attached to a bacterial protein portion. (After this gene has been constructed it is usually introduced into the bacterium by transformation with a compatible and replicable plasmid vector. Alternatively, the constructed gene can be inserted into the bacterial chromosome.) When the constructed gene is transcribed and as the protein of interest is formed it is transported to the periplasm via the bacterial transport mechanism discussed above. Recently, for example, the rat pre-proinsulin gene was inserted by recombinant DNA techniques into the *E. coli* β-lactamase gene [Villa-Komaroff, et al., Proc. Natl. Acad. Sci. USA 75: 3727-3731 (1978)]. β-lactamase is a periplasmic enzyme which, in its precursor form, carries a twenty-three amino acid leader sequence. The fusion protein resulting from the expression of the fused β-lactamase and pre-proinsulin genes was transported to the periplasm via the above-described normal transport mechanism.

European patent application No. 0,006,694, filed Apr. 6, 1979, listing Gilbert, et al. as inventors, discloses the production of such genetically-engineered fusion proteins by expression of DNA sequences having the gene coding for a "foreign" protein of interest attached to a DNA sequence coding for a leader sequence of a periplasmic protein. This procedure, however, merely provides a way to transport the protein of interest to the periplasmic space. The protein must still be extracted and isolated from this compartment. Gilbert, et al. also briefly mention attachment of the gene of interest to the leader sequence of a secretory, or extracellular, protein. In theory, in such an arrangement the protein of interest would be excreted beyond the periplasm into the fermentation medium. However, there are no known *E. coli* proteins which are externalized, that is, transported beyond the outer membrane.

U.S. Pat. No. 4,336,336, filed Jan. 12, 1979, listing Silhavy, et al. as inventors, discloses a method of producing fusion proteins which are transported into the outer membrane. This method provides for the fusion of a gene coding for a cytoplasmic bacterial protein with the gene for a non-cytoplasmic carrier protein thereby producing a fusion protein which is carried to the outer membrane. In addition, it is asserted that the method could be used to insert a "foreign" gene (e.g., coding for a eukaryotic protein) into the already constructed fusion gene.

However, as with the Gilbert, et al. invention discussed above, this method does not result in transportation of the protein of interest to the extracellular medium. Conventional extraction methods must still be employed to isolate the protein.

The conventional isolation of bacterial protein from the periplasm of gram-negative bacteria poses problems owing to the tough, rigid cell walls that surround these cells. The bacterial cell wall maintains the shape of the cell and protects the cytoplasm from osmotic pressures that may cause cell lysis; it performs these functions as a result of a highly cross-linked peptidoglycan (also known as murein) backbone which gives the wall its characteristic rigidity.

*E. coli* and the other gram-negative bacteria have a complex cell membrane structure. There is an outermost membrane exterior to the peptidogylcan layer of the cell wall. Interior to the peptidoglycan layer lies the cytoplasmic membrane. Between the outer and cytoplasmic membranes is an aqueous compartment, called the periplasm or periplasmic space, where certain enzymes and other proteins are located. Since these periplasmic proteins are located outside the cytoplasmic membrane they can be isolated without disrupting the cytoplasmic membrane and thus can be obtained relatively free from cytoplasmic contaminants. The selective extraction of these periplasmic proteins without release of cytoplasmic proteins, however, requires disruption of the cell wall, either by mechanical or chemical means while leaving the inner, or cytoplasmic, membrane intact. Thus, some means for removing the cell wall or increasing its permeability is necessary for isolation of the periplasmic proteins free from cytoplasmic contaminants.

A widely used technique of cell wall removal is enzymatic treatment of the cell culture with lysozyme which hydrolyzes the peptidoglycan backbone of the cell wall. The method was first developed by Zinder and Arndt [Proc. Natl. Acad. Sci. USA 42: 586-590 (1956)] who treated *E. coli* with egg albumin (which contains lysozyme) to produce rounded cellular spheres later known as spheroplasts. These structures retained some cell wall components but had large surface areas in which the cytoplasmic membrane was exposed. However, there are several disadvantages to use of the lysozyme method for isolating periplasmic proteins. Firstly, the cells must be treated with EDTA (ethylenediamine tetraacetic acid) or high pH, both of which tend to weaken them. Secondly, the method is not suitable for lysis of large amounts of cells because the enzyme is inefficient and there is difficulty in dispersing the enzyme throughout a large pellet of cells. Thirdly, since treatment with lysozyme results in the formation of spheroplasts, the treatment must be performed in an osmotic stabilizing solution to prevent lysis. In addition, attempts to culture spheroplasts indefinitely, in order to harvest protein excreted beyond the cytoplasmic membrane, would encounter problems of spheroplast stability.

Another method of extracting periplasmic proteins does not involve physical removal of the cell wall to expose the periplasm but rather entails subjecting the cells to a severe osmotic shock which causes the release of certain periplasmic proteins. The cells are placed in a hypertonic sucrose medium containing EDTA which causes them to lose water and shrink, the cytoplasmic membrane drawing away from the cell wall. The cells are then placed in a magnesium chloride "shock" solution which drastically decreases the osmotic pressure outside the cell causing water to rush into the cell which swells the cell and seems to propel the periplasmic proteins to the exterior of the outer membrane. It should be noted that while EDTA increases permeability of the membrane surface in *E. coli*, it will not by itself cause release of periplasmic enzymes; rather, both osmotic shock and EDTA treatment are necessary. Moreover, it would be extremely difficult to shock large amounts of cells.

Many other methods which totally disrupt cells are non-selective for periplasmic proteins.

Lastly, *E. coli* mutants that leak various periplasmic enzymes have been isolated. For example, Lopes, et al. [J. Bacteriol. 109(2): 520-525 (1972)] treated *E. coli* cells with a mutagen such as nitrosoguanidine and mutants excreting periplasmic enzymes were selected by enzyme assay systems. Such mutants included those leaking ribonuclease I, endonuclease I and alkaline phosphatase. It is believed that these mutants are deficient in some component of the outer bacterial membrane leading to an increase in the cells' permeability. In addition, several excreted periplasmic proteins have been separated from the culture medium by antibody precipitation or SDS-polyacrylamide gel electrophoresis in order to characterize these "periplasmic leaky" mutants [see, for example, Anderson, et al., J. Bacteriol. 140(2): 351-358(1979) and Lazzaroni and Portalier, J. Bacteriol. 145(3): 1351-1358 (1981)].

3. BRIEF SUMMARY OF THE INVENTION

The present invention involves use of a phage gene, or a fragment thereof, or any defective or mutant bacterial gene that causes changes in the outer membrane of gram-negative cells resulting in the leakage of proteins located in or transported to the periplasm. The invention applies to any gram-negative bacterium that produces proteins which are transported to the periplasmic space. The method of the invention allows selective isolation of proteins that locate in the periplasm without the need for lysozyme treatment, mechanical grinding or osmotic shock treatment of cells.

In one embodiment of the present invention, mutants that exhibit the above-described "periplasmic leaky" phenotype are isolated and utilized as a means for causing externalization of fusion proteins transported to the periplasm by genetic engineering techniques. While such "periplasmic leaky" mutants have been reported in the published literature, such mutants have never been utilized as a means for obtaining fusion proteins transported to the periplasm by genetic engineering techniques. Rather, the creation of these mutants appears to be directed at elucidation of the function and structure of the bacterial envelope and the location of various enzymes within the membrane structure.

While mutagenesis of cells to produce the "periplasmic leaky" phenotype may provide a means of isolating genetically engineered fusion proteins, this process is not ideal for such use. Treatment with a mutagen may decrease the viability of any survivor mutant. The existence of the "periplasmic leaky" mutation may be accompanied by other less desirable phenotypes such as temperature sensitivity of cell growth. In addition, once the desired mutation has occured, there is no way to control the expression of the mutation.

The preferred embodiment of the present invention provides a more practical, easily controlled method by which to increase the outer bacterial membrane permeability for the isolation of proteins in the periplasmic space. The fl bacteriophage gene III can be introduced into the cell on a plasmid or on the bacterial chromosome by standard and predictable genetic engineering methods. Furthermore, the subsequent expression of the gene in the form of gene III protein can be easily controlled, i.e., induced or suppressed, by the appropriate transcriptional and translational controls.

According to the preferred embodiment of the present invention, recombinant DNA techniques are utilized to insert the bacteriophage fl minor coat protein gene III, or the amino terminal-coding portion thereof, into a plasmid or into the bacterial chromosome such that the bacterial cell is capable of replicating and expressing the gene. Proper insertion of the phage gene III DNA sequence into an extrachromosomal plasmid causes production of gene III protein which in turn leads to an increase in the permeability of the outer membrane and thereby facilitates periplasmic protein isolation. Such extrachromosomal plasmids include compatible non-fd phage plasmids containing gene III or a fragment thereof. In addition, it may be possible to insert phage gene III DNA or a fragment thereof into the E. coli chromosome perhaps by the attachment of gene III to the lysogenizing phage λ). Thus, the gene III DNA sequence may be expressed in an E. coli cell capable of expressing a "foreign" DNA sequence (i.e., a DNA sequence coding for a protein not naturally found in E. coli) attached to a DNA sequence coding for a leader sequence of a periplasmic protein. The foreign protein is then synthesized in a novel precursor form. It is either attached directly to a bacterial leader sequence or to the amino terminal portion of a bacterial protein including a leader sequence and is transported to the periplasmic space where it is released in mature form or as a fusion protein. Owing to the presence and expression of the gene III DNA sequence, the foreign protein which has been transported to the periplasm is externalized into the fermentation medium without the need for using conventional cell disruption techniques. Thus, such cells can be continuously cultured and the externalized foreign protein collected from the culture medium.

It is to be understood that the gene III DNA sequence may be located on the same plasmid as the constructed gene coding for the leader sequence attached to the foreign protein, or the gene III DNA sequence may be on a different plasmid or on the bacterial chromosome. Moreover, gene III or its 5' fragments can have the gene for a foreign protein attached to it such that the gene III protein portion serves as a leader sequence.

Similarly, according to this preferred embodiment, naturally occurring bacterial periplasmic proteins may leak from the cell and be isolated as a result of the gene III protein membrane effect.

BRIEF DESCRIPTION OF THE DRAWINGS

The present invention can be more fully understood by reference to the following detailed description of the invention and the appended figures (not drawn to scale) in which.

4. DETAILED DESCRIPTION OF THE INVENTION

The present invention provides a simple method for the isolation of proteins transported to the periplasmic space in gram-negative bacteria and, in particular, E. coli and its relatives by the introduction into the cell of a phage gene protein (or a fragment thereof) or by the use of a bacterial periplasmic "leaky" mutant (defective in an outer membrane component) that increases the permeability of the outer bacterial membrane causing leakage of periplasmic proteins to the exterior of the cell. This invention can be used for the isolation of both genetically engineered fusion proteins which are transported to the periplasm and naturally occurring E. coli periplasmic proteins.

The method of this invention allows the isolation from the medium of genetically engineered fusion proteins expressed in cells when a "foreign" DNA sequence is attached to a bacterial leader sequence for a periplasmic protein. It may be necessary to have present on the carboxy terminus of the leader sequence some of the amino acids necessary for recognition by the bacterial enzyme(s) which cleaves the leader sequence during the transport process. The normal bacterial transport system then carries the fusion periplasmic protein to the periplasm where the action of gene III protein or a bacterial mutation allows externalization of the fusion protein into the culture medium. Expression of the fusion protein within the cell may be due to the insertion of the DNA sequence for the "foreign" protein into either the chromosome of the bacteria or into an extrachromosomal plasmid including one containing gene III sequences.

In the preferred embodiment of the invention, expression of gene III within the cell may be due to its insertion into either the bacterial chromosome, a plasmid bearing the fusion gene or any other extrachromosomal plasmid.

Although the isolation of genetically engineered fusion proteins may be accomplished by the use of a phage protein or a bacterial mutation either of which causes a membrane perturbation effect, the use of a relatively easily inserted phage DNA sequence causing such an effect is preferred.

In addition, according to this embodiment utilizing f1 gene III, naturally occurring bacterial periplasmic proteins (such as β-lactamase) leak out of the outer bacterial membrane into the fermentation medium and are more easily isolated therefrom than by the use of standard extraction procedures from whole cells.

As is more fully described below, the method of this invention may be carried out either by introduction of the entire gene III sequence into the cell or merely the amino terminal-coding portion of the gene (e.g., approximately the first 98 amino acids) to produce the desired disruptive effects on the bacterial outer membrane.

4.1 IDENTIFICATION AND ISOLATION OF GENE III

The method of this invention includes the identification, isolation and characterization of the filamentous phage f1 gene III DNA sequence in order that the gene may be inserted into a cloning vector prior to its introduction into the bacterial cell where it will be expressed.

The different genes carried on the phage genome were defined using complementation studies of various f1 mutants. In a complementation analysis, a bacterial culture is jointly infected with two phage mutants, each one alone being unable to produce phage progeny within the cell. If the mutant pair are now able to grow in the cell, they are said to complement each other, each one supplying the crucial function defective in the other. Thus, the respective mutations are in two different genes. Inability of the two to grow despite mixed infection indicates a common defect in a particular gene for which neither one can supply the proper protein. Physiological analysis has shown that gene III mutants are defective in attachment to new hosts, cause the production of polyphage, and have lesions which are reflected in the stability of the virion.

Figure 1:
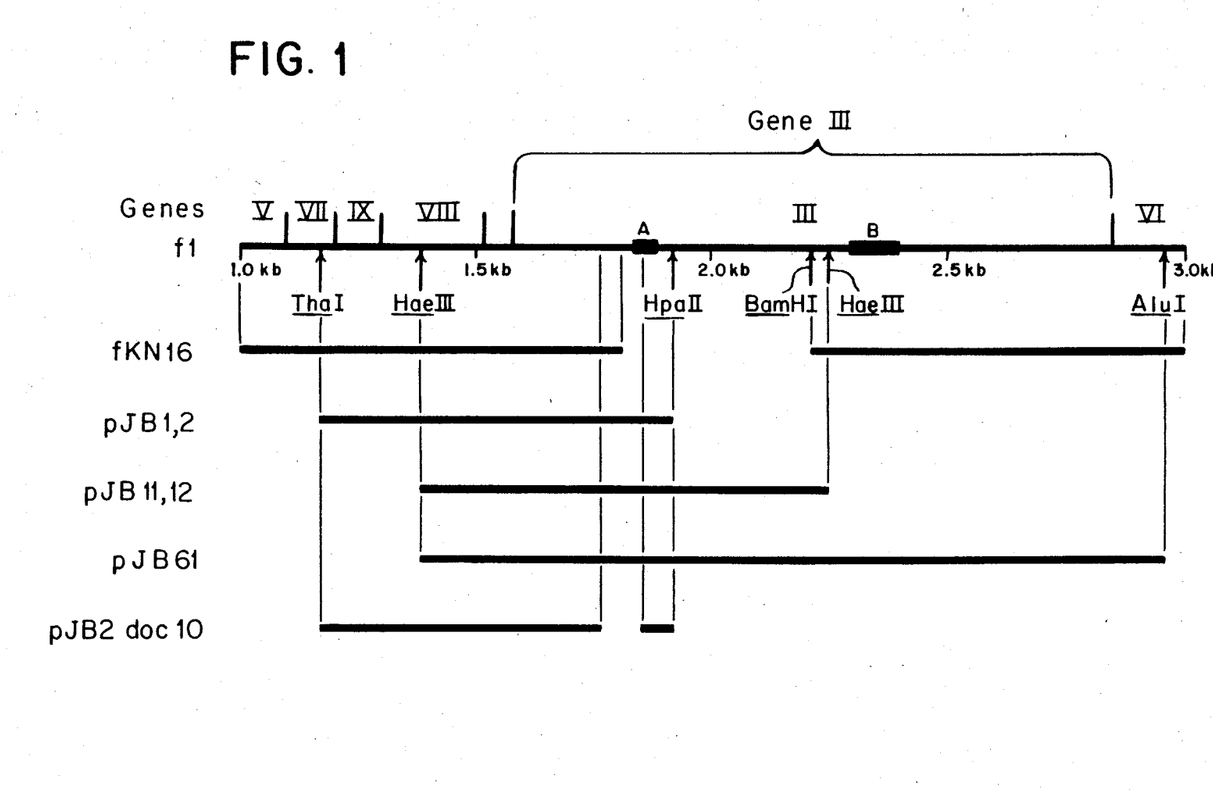
FIG. 1 represents a portion of the genetic and restriction maps of the filamentous fl bacteriophage, identifying the DNA sequence for gene III and related genes and indicating the locations along the genome where various restriction enzymes selectively cleave the DNA. The bars underneath the map represent the regions of the fl phage inserted into the designated plasmids or, in the case of fKN16, the phage genome of an fl deletion mutant. The darkened regions (labeled A & B) on the fl genome indicate the first and second glycine-rich regions, respectively.

To map gene III to a particular locus on the phage genome, genetic crosses are performed between various f1 mutants in mixed infections of bacterial cells and recombination frequencies are determined. Recombinants are phage progeny from a mixed infection which show genetic characteristics derived from both types of parental mutants. The lower the frequency of recombination, the closer two genes are on the genome. Thus, a genetic map based on recombination frequency can be constructed; gene III being a DNA sequence of approximately 1200 nucleotides with a pribnow box at nucleotide 10 and the appropriate set of nucleotides at 35 upstream. Gene III maps at position 1579 through 2851 on the phage genome (see FIG. 1). In addition, the 6400 nucleotides of the phage (and its relatives of the *Inoviridae* family including members of the fd phage group such as, for example, fd, M13 and f1 ) have been completely sequenced [Beck and Zink, Gene 16: 35–58 (1981)] and restriction maps (made using a variety of restriction enzymes that cut the phage genome at specific sequences) have been correlated with the genetic map (see FIG. 1). Given the nucleotide sequence of the genome and gene III's position on the restriction map, the DNA sequence specifying gene III or any part of it can be cut out of the genome by treatment with the appropriate restriction enzyme and readily isolated by standard techniques of gel electrophoresis.

4.2 INSERTION INTO A CLONING VECTOR

Once the phage DNA fragment containing gene III has been identified and isolated, it is inserted into a cloning vector or plasmid that will provide a means of replicating and expressing the gene within a cell into which the plasmid is introduced. Insertion of the fragment may be accomplished by either cleaving a plasmid vector with a restriction enzyme that produces cohesive termini complementary to those of the gene fragment (the same restriction enzyme being used for cleavage of both the phage and plasmid DNAs to produce complementary termini on both) or by modifying the termini of either or both so that they are complementary, allowing the complementary sequences to anneal and then ligating the resulting plasmid. Alternatively, DNA fragments can be inserted by A-T or G-C tailing or blunt-end ligation. The final product is a genetically engineered recombinant plasmid that contains the phage gene for gene III protein with appropriate transcriptional and translational controls.

Figure 2:
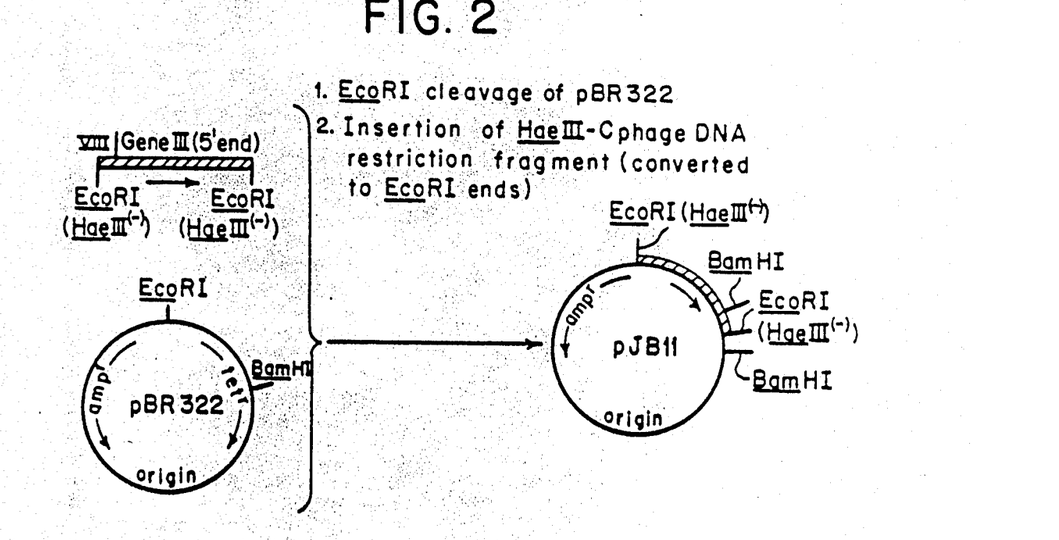
FIG. 2 indicates the procedure for insertion of a phage gene fragment coding for the amino terminal portion of gene III protein into plasmid pBR322 to form recombinant plasmid pJB11.

In the present invention, a portion of the gene III DNA sequence is inserted into pBR322 at the Eco RI site on the plasmid. The f1 bacteriophage DNA, isolated using the aforementioned techniques, is cleaved with Hae III, a restriction enzyme that in addition to other sites cuts the nucleotide sequence GG↓CC at position 1400 and 2241 on the phage genome and produces a fragment containing the amino terminal-coding portion of gene III (5' end) through codon 204 (see FIG. 1). This fragment is inserted into the Eco RI site on plasmid pBR322 by converting the Hae III cohesive termini on the fragment to Eco RI ends (by ligation to Eco RI linkers) and allowing the fragment to anneal with the complementary termini at the Eco RI site on the plasmid (the plasmid is cleaved with Eco RI at the sequence G AATTC and the phage fragment is inserted). The terminus converted from the Hae III to the Eco RI sequence is labeled Eco RI (Hae III$^{(-)}$). Optional alkaline phosphatase treatment of the plasmid prior to insertion of the fragment to remove the phosphate groups from the plasmid termini prevents re-formation of the plasmid as well as ligation of two plasmids to each other and assures ligation of the phage fragment to the plasmid. This plasmid which contains the portion of gene III from its putative promoter region through codon 204 is called pJB11 (FIG. 2). Experimental data indicates that this portion of the phage gene III is responsible for the leakage of periplasmic proteins from the cell and for other bacterial outer membrane disturbances since E. coli transformants containing pJB11 exhibit these effects while E. coli cells containing pBR322 do not.

Figure 3:
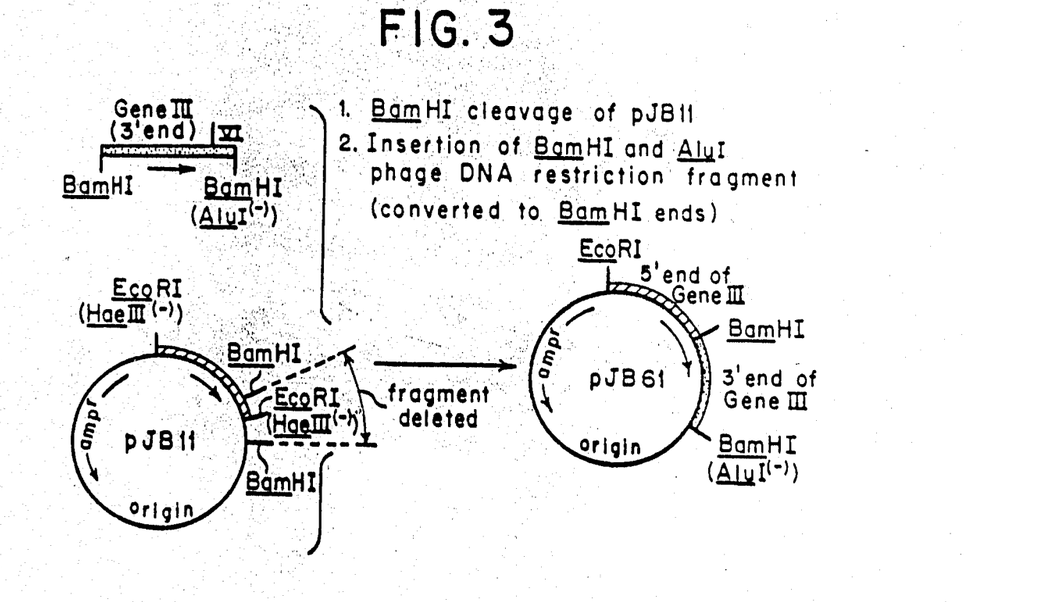
FIG. 3 indicates the procedure for insertion of a phage gene fragment coding for the carboxy terminal portion of gene III protein into plasmid pJB11 to form recombinant plasmid pJB61.

It is also possible to construct a plasmid bearing the DNA sequence for the entire gene III. The phage DNA is cleaved with the Bam HI restriction enzyme which cuts the sequence G↓GATCC at position 2220 within gene III and with the Alu I restriction enzyme which cuts the sequence AG↓CT at position 2963. The resulting DNA fragment contains the carboxy terminal-coding portion of gene III (3' end) and bears a Bam HI cohesive terminus at one end and an Alu I terminus at the other. The Alu I end of the fragment is ligated to a Bam HI linker and cleaved with Bam HI to produce a similar fragment, now with Bam HI cohesive termini at both ends. [The converted terminus is called Bam HI (Alu I(−)).] See FIG. 3. Plasmid pJB11 (already containing the amino terminal-coding portion of gene III) is then cleaved with Bam HI. Since this plasmid contains two Bam HI sites—one on the phage gene III insert (near the Eco RI site) and very near to its right end (3' terminus) and one on the plasmid within the tetracycline resistance gene, a 375 base pair fragment with some sequences of gene III but mostly pBR322 sequences is excised. The phage fragment coding for the carboxyl end of gene III protein (now with Bam HI cohesive termini) is allowed to anneal to the plasmids Bam HI termini and the DNAs are ligated (see FIG. 3). The resultant plasmid, pJB61, therefore, carries the entire phage gene III DNA sequence with its single Bam HI site. E. coli cells transformed with this plasmid produce gene III protein and exhibit its characteristic outer membrane effects including periplasmic protein leakage.

Once the phage gene or the amino terminal-coding portion thereof is inserted into the plasmid, host E. coli cells are transformed with the recombinant plasmid by techniques well known in the art. The transformed cells are then selected based upon the expression of gene markers present on the plasmid such as antibiotic resistance. Expression of such marker proteins indicates that the plasmid is intact and is replicating. Alternatively, phage gene III may be inserted into the genome of the bacteria by techniques well known in the art.

4.3 EXPRESSION OF GENE III

Gene III is expressed in phage infected cells as well as in cells into which the phage gene has been inserted via genetic engineering techniques. Sequencing of phage DNA has shown that the phage gene III sequence codes for a 406 amino acid membrane protein that contains two glycine-rich domains (indicated by broad darkened regions on the f1 genome of FIG. 1) and bears an 18 amino acid signal peptide (leader sequence) which is normally cleaved before the protein is assembled into virus particles at the E. coli membrane. The protein forms a minor component of the virion particle and is responsible for the infectivity of the bacteriophage. It is found in the membrane fraction of the infected cells and appears to be localized primarily in the cytoplasmic membrane to which it is anchored by its highly hydrophobic carboxy terminal end.

Although phage infection of cells involves, to some extent, expression of gene III protein, mere infection of cells with the phage does not cause substantial externalization of proteins owing to insufficient amounts of gene III protein. (Experimental evidence indicates that the outer membrane effect of phage infected cells is more than 100-fold less than the effect noted upon insertion of gene III into the cell by genetic engineering methods.) Therefore, phage infection of cells would not be an ideal method for isolating externalized proteins. In any event, phage infected cells are impractical for use in isolating externalized proteins for several other reasons. Firstly, phage infection decreases the viability of the cells. Secondly, such infection distorts the synthetic mechanism of the cell, decreasing synthesis of cellular components such as the fusion protein of interest while enhancing phage protein synthesis.

Transformation of E. coli cells with recombinant plasmids bearing gene III and selection of cells carrying functioning replicating plasmids (usually by antibiotic resistance, the gene for which is known to be carried on the plasmid) allows the cultivation of a population of cells expressing the gene. These recombinant DNA techniques can therefore be used to produce the gene III protein in E. coli cells without the adverse effects of phage infection. Likewise, these techniques can be utilized to introduce into the cell varying portions of gene III (as in pJB11) in order to determine which segment of the gene is responsible for a given effect.

The present invention focuses on the disruptive effect of gene III protein on the bacterial outer membrane. Experiments utilizing various recombinant plasmids bearing different segments and mutations of the gene III DNA sequence demonstrate that the expression of only the amino terminal portion of the gene III protein is necessary in order to produce the desired effect in the cell. Firstly, cells transformed with recombinant plasmids, pJB1,2 and pJB11,12 (containing only the 5' region of the gene) show the same membrane effects as cells transformed with pJB61 (containing the entire gene sequence). Secondly, deletion mutations in the amino terminal-coding portion of gene III abolish the observed effects of the protein (see fKN16 of FIG. 1). Thirdly, cells with plasmids bearing an amber mutation at codon 21 of gene III exhibit none of the perturbed membrane effects in non-suppressing hosts. The effects are restored, however, in suppressing hosts. Lastly, cells transformed with plasmid pJB2doc10 which bears a deletion mutation of a portion of gene III coding for part of the first glycine-rich domain of gene III protein do not exhibit the membrane effects (see pJB2doc10 of FIG. 1). The first glycine-rich domain is within the first 98 amino acids of gene III protein. These findings pinpoint at least the amino terminal 98 amino acids of gene III protein as the cause of the observed effects.

It should be noted that since gene III protein is normally bound to the cytoplasmic membrane via its carboxyl terminus, production of only the amino portion of the protein results in a truncated protein found "free floating" in the periplasm which escapes into the medium. Nevertheless, the effects of the truncated protein are the same as the full length protein.

4.4 EFFECTS OF GENE III EXPRESSION

The expression of gene III in *E. coli* cells causes a number of effects on the outer membrane of the bacteria.

4.4.1 INCREASED COLICIN TOLERANCE

Cells expressing gene III exhibit an increased tolerance to certain colicins which are bactericidal proteins produced by certain strains of bacteria against other strains. *E. coli* cells transformed with gene III-containing recombinant plasmids show a greater than ten-thousand-fold increase (over non-transformed cells) in tolerance to colicin E1 and K, which act on the cell membrane and colicin E3, which acts on the ribosomes and only a slight increase in tolerance to colicin E2, which acts on the DNA. Thus, a general tolerance to group A colicins is expressed by these transformants due to the presence of gene III protein.

4.4.2 INCREASED DEOXYCHOLATE SENSITIVITY

*E. coli* cells transformed with gene III-bearing plasmids exhibit an increased sensitivity to detergents such as deoxycholate. Thus, when transformed cells are plated in agar containing 1.5% sodium-deoxycholate, they are unable to form colonies.

This increased deoxycholate sensitivity is indicative of an outer membrane defect since it is believed that detergents such as deoxycholate act to disrupt cell membranes and allow leakage of cellular components, probably by the interaction of the hydrophobic hydrocarbon chain of the detergent with the membrane lipid coupled with the interaction of a hydrophilic anion or cation on the detergent with protein in the membrane. In addition, both spheroplasts and outer membrane mutants show such deoxycholate sensitivity. Thus, gene III protein present in these cells appears to disrupt the outer membrane leading to an enhanced effect by detergents. This property of cells containing gene III-bearing plasmids is useful for monitoring gene III expression.

4.4.3 DECREASED ABILITY TO FORM FUNCTIONAL F-PILI

The F-pilus is a long, thin appendage on the surface of male bacteria (bacteria carrying the sex factor, F) that has been implicated in both the process of adsorption of phage during infection of the bacteria as well as the process of conjugation (the transfer of genetic material from one bacterium to another). Any defect in the cell's ability to form or utilize this surface structure therefore would be expected to affect phage infectivity and conjugation.

Experimental evidence indicates that the expression of gene III has an effect on these two bacterial functions and suggests that gene III protein causes some defect in the F-pilus. *E. coli* cells expressing gene III are resistant to male-specific phages (which adsorb onto the F-pilus during infection). This includes resistance to superinfection by f1 bacteriophage. They are also completely resistant to killing by R84, an f1 "killer" amber mutant (in gene VII). Non-transformed cells die shortly after infection with R84 whereas transformed cells survive. Experiments demonstrating that transformed cells could be transfected by f1 DNA indicate that the resistance to f1 infection may be due to a membrane defect which prevents the usual adsorption of the phage. In addition, cells carrying fKN16, a mutant of the related phage fd bearing a deletion including the entire first glycine-rich domain in gene III (see FIG. 1), can be superinfected. This shows gene III to be responsible for the superinfection resistance of cells expressing the gene.

In addition, cells expressing gene III demonstrate a decreased efficiency as conjugal donors compared to non-transformed cells. The F-pilus plays a role in the transfer of genetic material from the male bacterium containing the F factor to the female bacterium (lacking the factor) and so a decreased ability to perform this transfer due to the presence of gene III protein points to a defect in the F-pilus at the cell surface.

4.4.4 LEAKAGE OF PROTEINS FROM THE PERIPLASM

*E. coli* cells carrying the phage gene III or the amino terminal-coding portion thereof leak significant amounts of $\beta$-lactamase, a periplasmic protein, to the exterior of the cell. $\beta$-lactamase is an enzyme produced by a number of penicillin-resistant bacteria. The enzyme, the gene for which is found on a plasmid in *E. coli*, produces the bacterial resistance to penicillin by splitting the $\beta$-lactam ring of the molecule to form penicilloic acid.

When ampicillin-resistant *E. coli* cells are transformed with gene III plasmids and plated with ampicillin-sensitive cells on ampicillin plates, it was found that the gene III-containing cells were surrounded by a large halo of ampicillin-sensitive cells (i.e., the ampicillin-sensitive cells in the area of the halo were not killed). This effect was due to the leakage from the gene III-containing cells of $\beta$-lactamase which degrades the ampicillin, a semi-synthetic drug sensitive to $\beta$-lactamase. Thus, cells expressing gene III cross-protect neighboring ampicillin-sensitive cells from the drug due to leakage of the periplasmic $\beta$-lactamase enzyme from the cell.

This cross-protection is not found with *E. coli* cells carrying the non-recombinant plasmid pBR322. In addition, transformed cells carrying mutations in the gene III region show no cross-protection. Therefore, the aggregate of evidence showing other membrane defect phenotypes such as increased colicin tolerance, increased deoxycholate sensitivity, decreased ability to form F-pili for conjugation, and resistance to superinfection upon introduction of gene III into the cell points to the presence of gene III as the cause of the leakage of periplasmic proteins as well. In addition, all these effects have been observed in cells transformed with recombinant plasmids pJB11,12 and pJB1,2, which carry only the amino terminal-coding portion of gene III. Therefore, the amino part of the protein alone is sufficient to establish the outer membrane perturbation necessary for the leakage and isolation of periplasmic proteins Cytoplasmic proteins such as $\beta$-galactosidase do not leak from gene III-containing cells. It appears, therefore, that this leakage occurs due to a selective effect on the outer bacterial membrane with no similar effect on the cytoplasmic membrane.

An *E. coli* strain, K-38, carrying the pJB61 plasmid described herein has been deposited with the American Type Culture Collection, Rockville, Md. and has been assigned accession number 39162. A culture of the deposited microorganism will be made available to the public upon the grant of a patent based upon the present application. It is to be understood that the availability of a deposit does not constitute a license to practice the subject invention in derogation of patent rights granted by the United States government. Furthermore, the present invention is not to be limited in scope by the microorganism deposited, since the deposited embodiment is intended as a single illustration of one aspect of the invention. Indeed, various modifications of the invention in addition to those shown and described herein will become apparent to those skilled in the art from the foregoing description. Such modifications are intended to fall within the scope of the appended claims.

What is claimed is:

1. A method for facilitating externalization of proteins transported to the periplasmic space of an *E. coli* bacterium, comprising:

culturing in an appropriate culture medium an *E. coli* bacterium containing (a) an f1 bacteriophage gene III or gene III fragment coding or gene III protein or a polypeptide fragment thereof capable of causing a perturbation of the outer membrane of the bacterium such that other proteins transported to the periplasmic space selectively leak from the bacterium and (b) a first DNA sequence coding for the other protein operatively attached to a second DNA sequence coding for a suitable leader capable of mediating transport of the other protein to the periplasmic space, wherein the bacterium is capable of replacing the gene III or gene III fragment and the DNA sequences, and is capable of expressing sufficient amounts of the gene III protein or polypeptide fragment thereof to cause the perturbation, and wherein the other protein is a genetically engineered fusion protein.

2. The method of claim 1, wherein the first and second DNA sequences are located on a plasmid and the gene III or gene III fragment is located on the same plasmid.

3. The method of claim 1, wherein the first DNA sequence coding for the other protein is located on a plasmid and the gene III or gene III fragment is located on a different plasmid.

4. The method of claim 1, wherein the gene III or gene III fragment serves as the second DNA sequence coding for a suitable leader.

5. The method of claim 1, wherein the gene III fragment comprises the fragment of phage f1 gene III coding for the amino terminal portion of gene III protein.

6. The method of claim 1, wherein the gene III fragment comprises the fragment of f1 gene III coding for approximately the 98 amino terminal amino acids of gene III protein.

7. The method of claim 1, wherein the gene III or gene III fragment is introduced into the bacterium on a recombinant vector.

8. The method of claim 1, wherein the gene III or gene III fragment is introduced into the bacterium on a recombinant plasmid.

9. The method of claim 1, wherein the gene III or gene III fragment is introduced into the bacterium by infection with a non-fd phage.

10. The method of claim 1, wherein the gene III or gene III fragment is introduced into the bacterium by incorporation into the bacterial chromosome.

11. A method for facilitating externalization of proteins from the periplasmic space of an *E. coli* bacterium comprising:

introducing into the bacterium an f1 bacteriophage gene III fragment coding for a gene III polypeptide fragment capable of causing a perturbation of the outer membrane of the bacterium such that other proteins located in the periplasmic space selectively leak from the bacterium, wherein the bacterium is capable of replicating the gene III fragment and is capable of expressing sufficient amounts of the gene III polypeptide fragment to cause the perturbation.

12. The method of claim 11, wherein the other proteins are naturally occuring periplasmic proteins.

13. The method of claim 11, wherein the gene III fragment comprises the fragment of phage f1 gene III coding for the amino terminal portion of gene III protein.

14. The method of claim 11, wherein the gene III fragment comprises the fragment of the gene III coding for approximately the 98 amino terminal amino acids of gene III protein.

15. The method of claim 11, wherein the gene III fragment is introduced into the bacterium on a recombinant vector.

16. The method of claim 11, wherein the gene III fragment is introduced into the bacterium on a recombinant plasmid.

17. The method of claim 11, wherein the gene III fragment is introduced into the bacterium by infection with a non-fd phage.

18. The method of claim 11, wherein the gene III fragment is introduced into the bacterium by incorporation into the bacterial chromosome.

19. A method for isolating proteins externalized from an *E. coli* bacterium, comprising:

(a) culturing in an appropriate culture medium an *E. coli* bacterium containing (i) an f1 bacteriophage gene III or gene III fragment coding for gene III protein or a polypeptide fragment thereof capable of causing a perturbation of the outer membrane of the bacterium such that other proteins transported to the periplasmic space selectively leak from the bacterium and (ii) a first DNA sequence coding for said other protein operatively attached to a second DNA sequence coding for a suitable leader capable of mediating transport of said other protein to the periplasmic space; and (b) isolating the leaked proteins from the culture medium.

20. A method isolating proteins externalized from an *E. coli* bacterium, comprising:

(a) culturing in an appropriate culture medium an *E. coli* bacterium containing an f1 bacteriophage gene III or gene III fragment coding for gene III protein or a polypeptide fragment thereof capable of causing a perturbation of the outer membrane of the bacterium such that other proteins located in the periplasmic space selectively leak from the bacterium, wherein said bacterium is capable of replacing said gene III or gene III fragment and is capable of expressing sufficient amounts of said gene III protein or a polypeptide fragment thereof to cause said perturbation; and (b) isolating the leaked proteins from the medium.

* * * * *

UNITED STATES PATENT AND TRADEMARK OFFICE
CERTIFICATE OF CORRECTION

PATENT NO. : 4,595,658

DATED : June 17, 1986

INVENTOR(S) : ZINDER ET AL.

It is certified that error appears in the above-identified patent and that said Letters Patent is hereby corrected as shown below:

Col. 13, line 18, change "or" to --for--;

Col. 13, line 29, change "replacing" to --replicating--;

Col. 14, line 52, after "method" insert --for--;

Col. 14, lines 61-62, change "replacing" to --replicating--;

Signed and Sealed this

Tenth Day of February, 1987

Attest:

DONALD J. QUIGG

Attesting Officer

Commissioner of Patents and Trademarks